United States Patent [19]

Van Wijngaarden et al.

[11] Patent Number: 5,183,822
[45] Date of Patent: Feb. 2, 1993

[54] SUBSTITUTED 3,4-ANNELATED BENZIMIDAZOL-2(1H)-ONES

[75] Inventors: Ineke Van Wijngaarden; Derk Hamminga; Wouter Wouters, all of Weesp, Netherlands

[73] Assignee: Duphar International Research B.V., Weesp, Netherlands

[21] Appl. No.: 631,957

[22] Filed: Dec. 21, 1990

[30] Foreign Application Priority Data

Dec. 27, 1989 [NL] Netherlands ............. 8903157

[51] Int. Cl.[5] .................. A61K 31/46; C07D 519/00
[52] U.S. Cl. ............................ 514/305; 546/133; 546/137
[58] Field of Search ............. 546/133, 137; 514/305

[56] References Cited

U.S. PATENT DOCUMENTS 4,985,420 1/1991 Hamminga et al. ............ 514/211

FOREIGN PATENT DOCUMENTS 0336466 10/1989 European Pat. Off. .
14347 11/1990 PCT Int'l Appl. ............. 546/133

Primary Examiner—Marianne M. Cintins
Assistant Examiner—Catherine Scalzo
Attorney, Agent, or Firm—Stevens, Davis, Miller & Mosher

[57] ABSTRACT

The present invention is concerned with compounds of formula 1

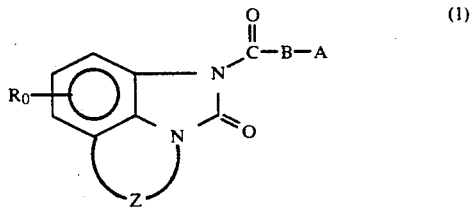

wherein
$R_0$ is alkyl, alkoxy or alkylthio having 1-4 carbon atoms, hydroxy, halogen,
Z, together with the carbon atom and the nitrogen atom and the intermediate carbon atom, constitutes a heterocyclic group which consists of 5-8 ring atoms, in which, besides the already present nitrogen atom, a second hetero atom from the group N, O, or S may be present, which ring may be substituted with 1-4 methyl group, or which ring may be annelated with a phenyl group optionally substituted with fluorine, or a methyl or methoxy group;
A is a group of formula 2 or 3

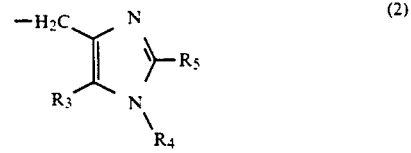

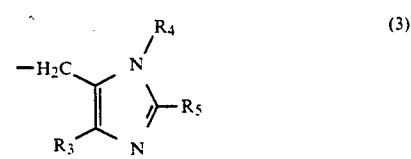

wherein one of the groups $R_3$, $R_4$ and $R_5$ is hydrogen, alkyl having 1-6 carbon atoms, cycloalkyl having 3-7 carbon atoms, alkenyl having 2-6 carbon atoms or phenyl alkyl having 1-3 carbon atoms in the alkyl group, and the two other groups independently of each other are hydrogen or alkyl having 1-4 carbon atoms, or wherein A is a polycyclic ring system in which one carbon atom is replaced by a tertiary nitrogen atom, for example, a ring system of formula 4, 5 or 6,

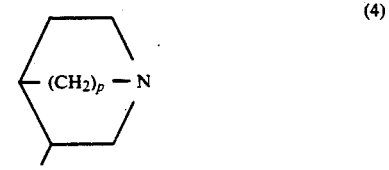

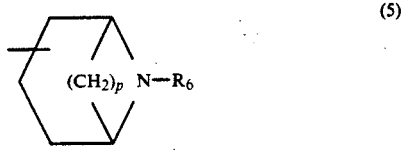

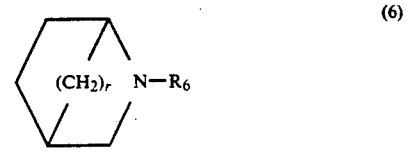

wherein p is an integer having the value 1 or 2, q is an integer having the value 2, 3 or 4, r is an integer having the value 1, 2 or 3, and $R_6$ is alkyl having 1-4 carbon atoms, cycloalkyl having 3-6 carbon atoms, cyclopropylmethyl, allyl, propargyl or benzyl, and
B is an oxygen atom or a group =N—R, wherein R is hydrogen, alkyl having 1-6 carbon atoms or benzyl, or wherein
B-A represents a group of formula 7

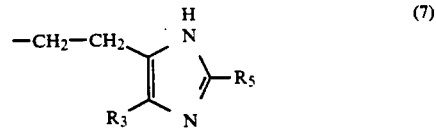

wherein $R_3$ ans $R_5$ having the meanings defined above, and the pharmaceutically acceptable acid addition salts thereof, which are pharmaceutically active as 5-HT receptor antagonists, and pharmaceutical products containing these compounds.

3 Claims, No Drawings

SUBSTITUTED 3,4-ANNELATED BENZIMIDAZOL-2(1H)-ONES

The invention relates to new heterocyclic compounds having an antagonistic activity on 5-hydroxytryptamine (5-HT) receptors to the preparation thereof and to pharmaceutical compositions which comprise such a new compound as an active substance.

European Patent Application No. 88830375.7 (publication No. 0309423) relates to a group of benzimidazoline-2-oxo-1-carboxylic acid derivatives which may be used as 5-HT receptor antagonists.

It has now been found surprisingly that compounds of formula 1

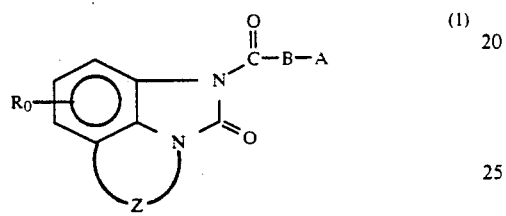

wherein $R_O$ is alkyl, alkoxy or alkylthio having 1–4 carbon atoms hydroxy, halogen, Z, together with the carbon atom and the nitrogen atom and the intermediate carbon atom, constitutes a heterocy clic group which consists of 5–8 ring atoms, in which, besides the already present nitrogen atom, a second hetero atom from the group N, O, or S may be present, which ring may be substituted with 1–4 methyl groups or which ring may be annelated with a phenyl group optionally substituted with fluorine, or a methyl or methoxy group;

A is a group of formula 2 or 3

wherein one of the groups $R_3$, $R_4$ and $R_5$ is hydrogen, alkyl having 1–6 carbon atoms, cycloalkyl having 3–7 carbon atoms, alkenyl having 2–6 carbon atoms or phenyl alkyl having 1–3 carbon atoms in the alkyl group, and the two other groups independently of each other are hydrogen or alkyl having 1–4 carbon atoms, or wherein A is a polycyclic ring system in which one carbon atom is replaced by a tertiary nitrogen atom, for example, a ring system of formula 4, 5 or 6,

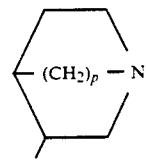

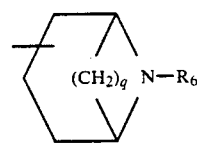

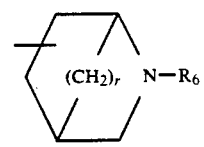

wherein p is an integer having the value 1 or 2, q is an integer having the value 2, 3 or 4, r is an integer having the value 1, 2 or 3, and $R_6$ is alkyl having 1–4 carbon atoms, cycloalkyl having 3–6 carbon atoms, cyclopropylmethyl, allyl, propargyl or benzyl, and B is an oxygen atom or a group =N—R, wherein R is hydrogen, alkyl having 1–6 carbon atoms or benzyl, or wherein B-A represents a group of formula 7

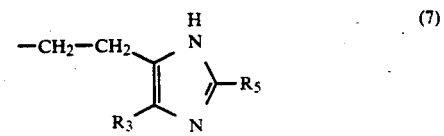

wherein $R_3$ and $R_5$ have the meanings defined above, and the pharmaceutically acceptable acid addition salts thereof have a similar activity, but are considerably more potent and longer active, and have a lower toxicity than the known compounds.

Suitable acids with which the compounds of formula 1 according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluene sulphonic acid, methane sulphonic acid, and the like.

One or more chiral centres may be present in the compounds of formula 1. Both the racemates and the separate enantiomers of compounds of formula 1 are included in the invention.

The antagonistic activity of the compounds of formula 1 on the 5-HT-induced response was determined and measured in the von Bezold-Jarisch reflex test in rats. The affinity to "neuronal" 5-HT receptors was determined and measured by the displacement of ($^3$H) GR65630 from rat entorhinal cortex membrane homogenate.

On the basis of the antagonistic activity on this type of 5-HT receptors the compounds may be used for the treatment of symptoms which are caused by overexcitation of the said receptors a) in the gastrointestinal system (nausea and vomitting as a result of exogenic factors, for example, cancer therapy, or endogenic factors, for example, stasis of the stomach and migraine), ulcer, dyspepsia, spasms, irritable bowel syndrome, etc., or b) in the central nervous system (hallucinations, delusions, mania, anxiety (in particular panic disorders, agoraphobia and obsessive compulsive disorders), depression, pain, improvement of the vigilance , etc.), or c) in the cardiovasular system, for example, spasms of the vessels, arrhythmia, etc. or d) in the respiratory system (including nasal disturbances and disturbances of bronchi and lungs), or e) for relieving or preventing withdrawal symptoms which are induced by drug abuse.

The compounds according to the invention and their salts may be brought into forms suitable for administration, for example, pills, tablets, coated tablets, capsules, powders, injection liquids, and the like by means of techniques conventionally used for this purpose and while using suitable auxiliary substances, for example, liquid or solid carrier materials.

The dosage in which the compounds according to the invention may be used depends on the severity and the nature of the disease to be treated and on the way of administration. As a rule the dosage will be between 0.05 and 20 mg, preferably between 0.1 and 10 mg of active substance daily.

The compounds of formula 1, wherein $R_O$, Z and A have the meanings mentioned hereinbefore and wherein B represents a group =N—R wherein $R_4$ is not a hydrogen atom, may be prepared by reaction of a compound of formula 8

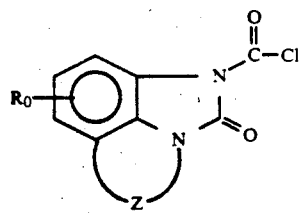

(8)

with an amine of the formula H—N(R)—A, wherein R and A have the above-mentioned meaning.

Compounds of formula 1, wherein A is a group of formula 2 wherein $R_3$ and $R_5$ have the above-mentioned meanings and $R_4$ is a hydrogen atom, may be obtained according to the above method by using as an amine a compound of formula 9 or 10

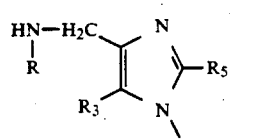

(9)

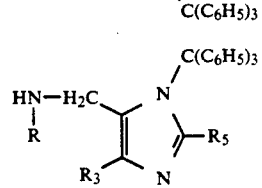

(10)

and then splitting off the triphenylmethyl group from the reaction product in acid conditions, for example, in a mixture of acetic acid and water.

The reaction of a compound of formula 8 with an amine of the formula H—N(R)—A is carried out in an organic solvent, for example, acetonitrile, chloroform, dimethylformamide, tetrahydrofuran, etc , in the presence of a base, for example, triethylamine or pyridine.

Compounds of formula 1, wherein B is oxygen can be prepared by reacting a compound of formula 11

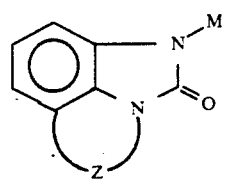

(11)

wherein M is an alkalimetal atom, with the appropiate chloroformic acid ester of formula 12

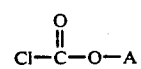

(12)

Compounds of formula 1 wherein B is $CH_2$ and A is a group of formula 2 or 3 and $R_4$ is hydrogen atom can be prepared by reacting a compound of formula 11 with a compound of formula 13 or 14

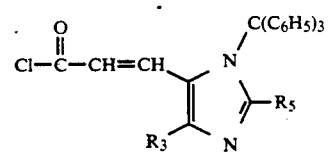

(13)

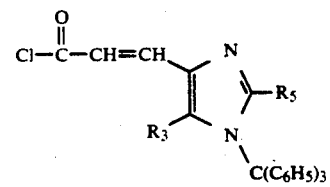

(14)

This coupling reaction preferably is carried out in DMF at a temperature of 0°-5° C. and is followed by reduction of the ethylene bond and removal of the tritylgroup under acid or reducing conditions.

The starting compounds of formula 8 used can be obtained by reaction of a compound of formula 15

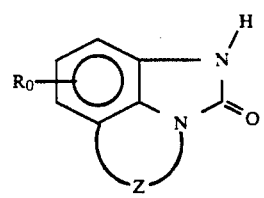

(15)

with phosgene, or di or triphosgene, in a solvent, for example, tetrahydrofuran.

The compounds of formula 15 can be prepared by methods known per se for analogous compounds.

A suitable method for the preparation of a compound 15 wherein. $R_O$ is a hydrogen atom and Z gives rise to six-membered heterocyclic group wherein the only hetero atom is one nitrogen atom (5,6-dihydro-4 H-imidazo [4,5,1-ij]quinoluin-2-(1H) one is described in C.A. 74, 53657d (1971)).

The corresponding compounds with seven-membered and eight-membered heterocyclic groups are prepared from the compounds of formula 16

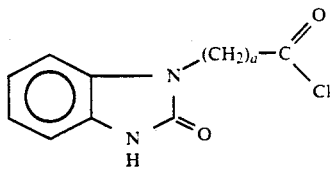
(16)

wherein a is an integer having the value 3 or 4, respectively by cyclization using aluminium trichloride in methylenechloride, followed by reduction of the resulting ketone (Huang-Minlon method).

The compounds of formula 11 can be converted into compounds of formula 13 using alkalimetalhydrides.

The compounds of formula H-N(R)-A and the chloroformic acid esters can be prepared by methods known per se.

The invention will now be described in greater detail with reference to the ensuing specific example.

EXAMPLE I

N-(endo-9-methyl-9-azabicyclo[3,3,1]non-3-yl)-5,6-dihydro-4H-imidazo[4,5,1-il]quinolin-2(1H)-one 1-carboxamide 2.5 g (14.4 mmol) of 5,6-dihydro-4H-imidazo[4,5,1-ij]quinolin-2(1H)-one together with 5.2 ml (43 mmol) of trichloromethyl chloroformiate in 100 ml of dry tetrahydrofuran was boiled while stirring for 6 hours. The mixture was then evaporated in vacuo. The residue was suspended in 30 ml of acetonitrile. 2.8 ml (20 mmol) of triethylamine and a solution of 2.3 g (14.8 mmol) of endo-3-amino-9-methyl- 9 azabicyclo[3,3,1]nonane in 25 ml of acetonitrile were then added dropwise successively. The mixture was stirred at room temperature for 2 hours and was then evaporated in vacuo. The residue was shaken with a mixture of 50 ml of 2N hydrochloric acid and 75 ml of ethyl acetate, after which filtering was carried out. The aqueous solution was washed with 75 ml of ethyl acetate, rendered alkaline with soda and shaken with methylene chloride. The methylene chloride layer was dried and evaporated in vacuo. The residue was chromatographed over silica gel using methylene chloride/methanol/ammonia (25%) in the ratio 90/10/1 as an eluent. After evaporating the desired fractions 0.62 g of the desired product were obtained having a melting-point of 164°–165° C.

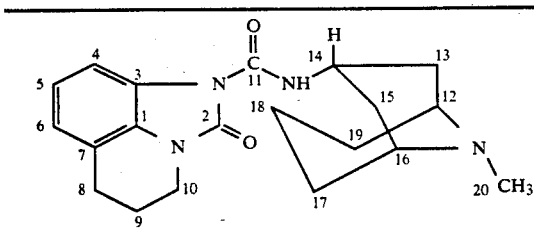

| C-13-NMR (SLV: CDCl₃. Ref. TMS) | | |
|---|---|---|
| 1 | 125.59 | S |
| 2 | 152.42 | S |
| 3 | 125.40 | S |
| 4 | 113.12 | D |
| 5 | 121.78 | D |
| 6 | 122.34 | D |
| 7 | 119.39 | S |

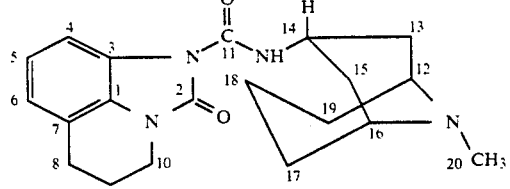

| C-13-NMR (SLV: CDCl₃. Ref. TMS) | | |
|---|---|---|
| 8 | 23.83 | T |
| 9 | 21.62 | T |
| 10 | 39.05 | T |
| 11 | 151.08 | S |
| 12 | 51.25 | D |
| 13 | 32.97 | T |
| 14 | 41.82 | D |
| 15 | 32.97 | T |
| 16 | 51.25 | D |
| 17 | 24.52 | T |
| 18 | 14.35 | T |
| 19 | 24.52 | T |
| 20 | 40.45 | Q |

According to similar methods the following compound was prepared:

N-(1-azabicyclo[2,2,2]oct-3-yl)-5,6-dihydro-4H-imidazo[4,5,1-ij]quinolin-2(1H)-one 1-carboxamide

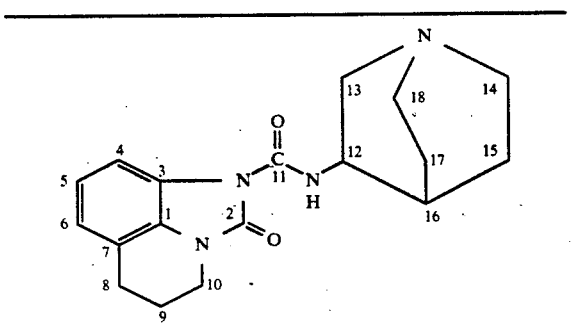

| C-13-NMR (SLV: CDCl₃ REF: TMS) | | |
|---|---|---|
| 1 | 125.61 | S |
| 2 | 152.46 | S |
| 3 | 125.21 | S |
| 4 | 112.96 | D |
| 5 | 121.98 | D |
| 6 | 122.48 | d |
| 7 | 119.59 | S |
| 8 | 23.80 | T |
| 9 | 21.59 | T |
| 10 | 39.10 | T |
| 11 | 151.59 | S |
| 12 | 47.15 | D |
| 13 | 56.24 | T |
| 14 | 47.39 | T |
| 15 | 25.71 | T |
| 16 | 25.86 | D |
| 17 | 20.26 | T |
| 18 | 46.63 | T |

EXAMPLE II 5,6-dihydro-4H-imidazo[4,5,1ij]quinolin-2(1H)-one 1-carboxylic acid (endo-8-methyl-8-azabicyclo [3,2 1]oct-3-yl) ester 0.6 g (13 mmol) of sodiumhydride (55% in oil) was added portion-wise to a solution of 1.74 g (10 mmol) of 5,6-dihydro-4H-imidazo[4,5,1-ij]quinolin-2(1H)-one in 30 ml of dimethyl formamide. After stirring during 10 minutes the mixture was cooled to 0° C., whereafter 1.7 g (7 mmol) tropine chloroformiate hydrochloride was added portion-wise. The reaction mixture was stirred succesively during half an hour at 0°-5° C. and during 16 hours at 20° C. Then, icewater was added and the mixture was shaken with methylene chloride. The methylene chloride layer was washed several times with water, and subsequently evaporated the residue was chromatographed on silica gel using methylene chloride/methanol/ammonia (90/10/1) as an eluent After evaporation of the selected fractions, 1.5 g of the crude desired product was obtained. By crystallisation of crude residue from acetonitril, 0.95 g of the desired product with a melting point of 217°-219° C. (decomposition) was obtained.

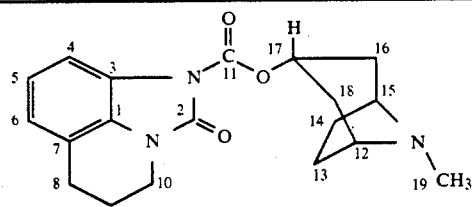

| C-13-NMR SLV: CDCl₃ REF: TMS | | |
|---|---|---|
| 1 | 126.45 | S |
| 2 | 150.66 | S |
| 3 | 124.96 | S |
| 4 | 112.26 | D |
| 5 | 121.84 | D |
| 6 | 122.44 | D |
| 7 | 119.36 | S |
| 8 | 23.83 | T |
| 9 | 21.49 | T |
| 10 | 39.08 | T |
| 11 | 149.64 | S |
| 12 | 59.81 | D |
| 13 | 25.40 | T |
| 14 | 25.40 | T |
| 15 | 59.81 | D |
| 16 | 36.59 | T |
| 17 | 71.17 | D |
| 18 | 36.59 | T |
| 19 | 40.47 | Q |

According to similar methods the following compound was prepared:
4,5,6,7-tetrahydro-imidazo[4,5,1-jk][1]benzazepin-2(1H)-one 1-carboxylic acid (endo-8-methyl-8-azabicyclo[3,2,1]oct-3-yl)ester.

| C-13-NMR SLV: CDCl₃ REF: TMS | | |
|---|---|---|
| 1 | 129.07 | S |
| 2 | 151.04 | S |
| 3 | 126.65 | S |
| 4 | 112.09 | D |
| 5 | 122.00 | D |
| 6 | 125.27 | D |
| 7 | 124.52 | S |
| 8 | 27.22 | T |
| 9 | 26.80 | T |
| 10 | 32.66 | T |
| 11 | 44.07 | T |

| -continued | | |
|---|---|---|
| C-13-NMR SLV: CDCl₃ REF: TMS | | |
| 12 | 150.51 | S |
| 13 | 59.70 | D |
| 14 | 25.50 | T |
| 15 | 25.50 | T |
| 16 | 59.70 | D |
| 17 | 36.74 | T |
| 18 | 71.49 | D |
| 19 | 36.74 | T |
| 20 | 40.58 | Q |

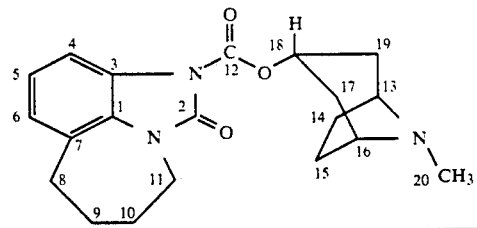

What is claimed is:

1. A 3,4-annelated benzimidazol-2(1H)-one 1-carboxylic acid derivative of formula (1):

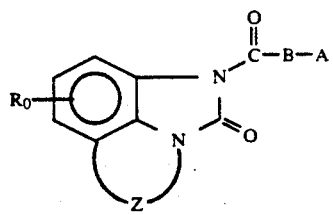

wherein
$R_0$ is hydrogen, alkyl, alkoxy or alkylthio having 1-4 carbon atoms, hydroxy, or halogen;
Z is ethylene or propylene, which may be substituted with 1-3 methyl groups,
A is a group of the formula (4):

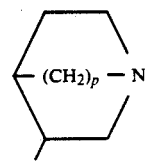

wherein p has the value 2, and
B is an oxygen atom or a group —N(R)—, wherein R is hydrogen, alkyl having 1-6 carbon atoms or benzyl;
or a pharmaceutically acceptable acid addition salt thereof.

2. A pharmaceutical compositon which comprises a pharmaceutically effective amount of a compound as claimed in claim 1 as an active substance together with a carrier.

3. A method of treating symptoms which are caused by overexcitation of 5-hydroxytryptamine receptors, wherein a pharmaceutically effective amount of a compound as claimed in claim 1 is administered to a patient in need thereof.

* * * * *